United States Patent [19]

Rzeszotarski et al.

[11] Patent Number: 4,644,003
[45] Date of Patent: Feb. 17, 1987

[54] 3-QUINUCLIDINOL ESTERS, USEFUL AS ANTAGONISTS OF MUSCARINIC ACETYLCHOLINE RECEPTORS

[75] Inventors: Waclaw J. Rzeszotarski, Washington, D.C.; Raymond E. Gibson, Arlington, Va.; William C. Eckelman, Rockville; Richard C. Reba, Potomac, both of Md.

[73] Assignee: Research Corporation, New York, N.Y.

[21] Appl. No.: 719,405

[22] Filed: Apr. 3, 1985

[51] Int. Cl.[4] .................. A61K 31/435; C07D 453/02
[52] U.S. Cl. .................................... 514/304; 546/137
[58] Field of Search ............... 546/137, 133; 562/470; 514/304

[56] References Cited

U.S. PATENT DOCUMENTS 3,714,357 1/1973 Gueremy et al. .................... 546/137

FOREIGN PATENT DOCUMENTS 0003422 12/1981 PCT Int'l Appl. ................ 546/137

Primary Examiner—Henry R. Jiles
Assistant Examiner—J. Richter
Attorney, Agent, or Firm—Scully, Scott, Murphy & Presser

[57] ABSTRACT

The present invention relates to antagonists of muscarinic acetylcholine receptors. More specifically, this invention contemplates highly selective antimuscarinic agents which are characterized as esters of 3-quinuclidinol and unsymmetrical alpha-disubstituted glycolic acids.

These highly selective antimuscarinic agents permit efficacy at particular sites designated $m_1$-AChR without affecting the muscarinic acetylcholine receptors of other tissues characterized by sites designated $m_2$-AChR. Such efficacy requires lower quantities of the antagonist thereby lowering toxicity and other undesirable side effects.

9 Claims, No Drawings

3-QUINUCLIDINOL ESTERS, USEFUL AS ANTAGONISTS OF MUSCARINIC ACETYLCHOLINE RECEPTORS

BACKGROUND OF THE INVENTION

The present invention relates to antagonists of muscarinic acetylcholine receptors which are designated m-AChR. More specifically, this invention contemplates highly selective antimuscarinic agents which are characterized as esters of 3-quinuclidinol and unsymmetrical alpha-disubstituted glycolic acids.

Stimulation of the parasympathetic nervous system is achieved organically through the release of acetylcholine and may be artificially induced, for example, by certain drugs classified as parasympathomimetics. The effects of such stimulation cover a myriad of physiological responses including dilation of blood vessels, decrease in heart rate, decrease in blood pressure, stimulation of gastrointestinal smooth muscle, increase in peristalsis, stimulation of smooth muscle in the bladder causing urination, contraction of bronchial smooth muscle and constriction of the pupil. This type of stimulation also has a pronounced effect on the endocrine system causing an increase in sweating, salivation, lacrymation and pancreatic secretion. These responses are initiated at the cellular level by the interaction between the acetylcholine molecule and particular neural receptor sites.

Antimuscarinic agents, otherwise known as cholinergic blockers, are known and have been used to effect the blockade of acetylcholine transmission to the muscarine receptor site thus having the effect of anesthetising the parasympathetic nervous system. The physiological consequence is to block the stimulation or induction of the aforementioned behavorial effects.

Antimuscarinics have been employed largely in general ophthalmological procedures, e.g., for pupil dilation and during ocular surgery. These drugs are also used for anesthetic premedication in order to prohibit excessive salivary and bronchial secretions and to prevent bronchial spasms and laryngoaspasms. The antisecretory action of these drugs make them useful in treating allergic reactions such as hay fever as well.

Some of the most important aspects of antimuscarinic agents are related to gastroenterology where they are used for the treatment of spastic colon, functional diarrhea, spastic constipation, cardiospasm, and some forms of colitis and peptic ulcers. Of course, these compounds are widely employed in cardiology.

For some time, it was believed by the pharmacological and medical professions that antimuscarinics exhibited very limited selectivity, with the major differences in these drugs being quantitative rather than qualitative. Clearly, this has been a substantial disadvantage in view of the range of physiological responses for which these agents can exhibit their influence. For this reason, the use of atropine, an atropa belladonna L. alkaloid, has remained the predominant anticholinergic antispasmodic.

However, recent pharmacological studies indicate that the m-AChR exhibit subclasses, designated $m_1$-AChR and $m_2$-AChR, respectively, i.e., with selective specificity, similar to those observed with the adrenergic, dopaminergic, histaminergic and opiate receptor systems.

In accordance with the present invention new highly selective muscarinic antagonists (to $m_1$-AChR) have been synthesized which enable efficacy at specified sites without affecting the sites of other tissues.

SUMMARY OF THE INVENTION

It is therefore one object of the present invention to provide novel antimuscarinic agents.

It is another object of this invention to provide novel antimuscarinic agents exhibiting high selectivity toward certain subclasses ($m_1$-AChR) of muscarinic acetylcholine receptors.

It is a further object of the present invention to provide a method for selectively affecting the parasympathetic nervous system.

Still another object of the present invention is to provide a method of affecting selected tissue and/or organs without affecting the m-AChR sites of other tissue during medical procedures requiring such anestheology.

These and other objects of this invention are accomplished herein by providing antimuscarinic agents of the following general formula:

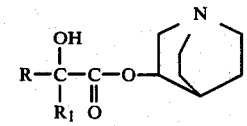

wherein R is phenyl, unsubstituted or substituted up to three substituents, including alkoxy, halogen, nitro, amino, alkylamino, dialkylamino, acylamino and trifluoromethyl; and wherein $R_1$ is hydrogen, alkyl, cycloalkyl, alkenyl, cycloalkenyl, alkynyl, alkyloxyalkyl, cycloalkyloxyalkyl, haloalkyl or haloalkenyl.

These compounds which are characterized as esters of 3-quinuclidinol and unsymmetrical alpha-disubstituted glycolic acids are effective in their pure or racemic forms and can be employed to selectively blockade certain subclasses of muscarinic acetylcholine receptors designated $m_1$-AChR without affecting the receptors of other tissue characterized by $m_2$-AChR. Moreover, due to this specificity, lower quantities of the compound are required to effect the desired results relative to conventional antimuscarinic agents thereby lowering toxicity and other undesirable side effects. Thus, this invention also contemplates the administration of an effective amount of the present compounds in a method for selectively antagonizing muscarinic acetylcholine receptors and can be conveniently employed for such purpose in pharmaceutically acceptable dosage forms.

DETAILED DESCRIPTION OF THE INVENTION

In accordance with the present invention, novel compounds have been synthesized which are useful as very selective antagonists of muscarinic acetylcholine receptors, i.e., blockers of acetylcholine receptor sites. These compounds permit selective efficacy at specific tissue characterized by $m_1$-AChR sites without effecting blockade at the muscarinic receptor sites of other tissue, i.e., $m_2$-AChR. The present compounds, which are characterized as esters of 3-quinuclidinol and unsymmetrical alpha-disubstituted glycolic acids, exhibit this selective efficacy in their pure (R,R), diastereomeric (R,R and R,S) and racemic forms.

More specifically, the compounds of the present invention have the following general formula:

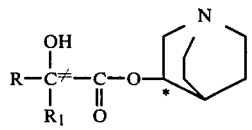

wherein R is phenyl, unsubstituted or substituted with up to three substituents including alkoxy, halogen, nitro, amino, alkylamino, dialkylamino, acylamino and trifluoromethyl; and wherein $R_1$ is hydrogen, alkyl, cycloalkyl, alkenyl, cycloalkenyl, alkynyl, alkyloxyalkyl, cycloalkyloxyalkyl, haloalkyl or haloalkenyl; * indicates a chiral center; and ≠ indicates a prochiral center (chiral if R≠$R_1$).

The preferred compounds are classified as 3-quinuclidinyl alpha-alkyl mandelates wherein R is phenyl as defined above and $R_1$ is hydrogen, methyl, ethyl or propyl. The most preferable of the compounds is the alpha-alkyl mandelate, 3-quinuclidinyl atrolactate (QNA), wherein $R_1$ is methyl.

As indicated by the above formula of the present compounds, R is phenyl and may be substituted with one, two or three substituents such as alkoxy, halogen, trihalomethyl, alkylamino, dialkylamino, alkylamides and similar such groups.

As further indicated by the above representative formula, $R_1$ can be hydrogen, alkyl, cycloalkyl, alkenyl, alkynyl, cycloalkenyl, cycloalkyloxyalkyl, alkoxylalkyl, haloalkyl and haloalkenyl.

The alkyl groups either alone or within the various substituents defined hereinbefore are preferably lower $C_1$–$C_3$ alkyl and include methyl, ethyl, propyl or isopropyl. The alkyl groups in the alkoxy derivatives are also selected from the above list.

The alkenyl groups either alone or within the various substituents include ethenyl, propylenyl or isopropylenyl.

The alkynyl groups either alone or within the various substituents include ethynyl or propynyl.

The cyclic group includes cyclopropyl. The cycloalkene include cyclobutene, cyclopentene, cyclohexene. The cyclic groups may be unsubstituted or substituted with alkyl groups, which have been defined hereinabove.

The halo atoms in halo and trihalo methyl, and haloalkenyl are Cl, Br, I and F.

The preferred substituents for R are methoxy, iodo, chloro, bromo, fluoro, diethylamino, acetamido, propionamido and trifluoromethyl.

The preferred substituents for $R_1$ are methyl, ethyl, propyl, cyclopropyl, prop-2-enyl, propynyl, methoxymethyl, cyclopropyloxymethyl, and 2- or 3-fluoroprop-2-enyl. The most preferred $R_1$ substituent is methyl.

The compounds of this invention can exist as optical isomers and therefore include both racemates of the isomers, the individual isomers and mixtures of the isomers. The racemates are easily separated through conventional means.

The present compounds are prepared by any one of three general procedures. First, by the treatment of alpha-ketocarboxylic acid ester of 3-quinuclidinyl of the formula:

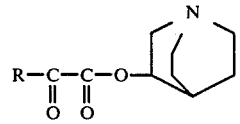

with reagents such as $R_1$MgHal, $R_1$Li, $R_1$Hal/Zn or the like wherein $R_1$ is the same as defined above. Second, the present compounds can be prepared by treatment of the ketone having the formula:

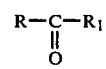

with trimethylsilyl cyanide (TMSCN) followed by hydrolysis of the cyanohydrin to obtain an acid having the formula:

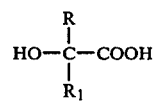

wherein R and $R_1$ are the same as defined above. The acid is subsequently treated with acetic anhydride to produce the acetyloxy intermediate which in turn is coupled with the 3-quinuclidinol in the presence of a suitable carbodiimide, followed by NaSH hydrolysis of the acetyloxy group.

Finally, these compounds can be prepared by the treatment of the above acid with diazomethane or an ethanol/triflic acid anhydride mixture followed by transesterification of the obtained esters with 3-quinuclidinol in the presence of sodium, potassium or lithium to form a 3-quinucldinylate as shown in Scheme I below:

Scheme I

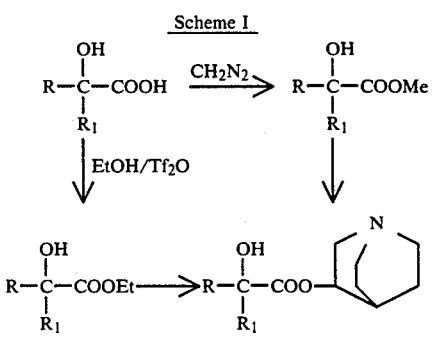

Synthesis of the present compounds are carried out utilizing water or any inert organic solvent as a diluent. Preferred organic solvents include, for example, alcohols such as methanol, ethanol and propanol, halocarbons such as methylene chloride, chloroform and carbon tetrachloride, benzene, toluene, esters such as ethyl acetate, ethers such as ethyl ether and dioxane. The reaction temperatures can be varied over a substantial range from about 80° C. to about 200° C.

Surprisingly, it has been discovered that the compounds of the present invention and preferably the compound 3-quinuclidinyl atrolactate (QNA) exhibit high affinity for the $m_1$-AChR subclass and therefore can be utilized to selectively blockade the acetycholine effect of particular cell sites without inducing the blockade effect in other tissue characterized by $m_2$-AChR.

Specifically, the present compounds successfully blockade the muscarinic receptors characteristically found in caudate/putamen cells and which are representative of the $m_1$-AChR-type muscarinic receptors to a significantly greater extent, better than twenty-five times (see Table I below), than muscarinic receptors from, for example, ventricular muscles ($m_2$-AChR-types). Comparison with non-selective conventional antimuscarinics such as 3-quinuclidinyl benzilate (QNB) clearly elucidate the selectivity of the present compounds as shown in Table I.

Thus, for example, a patient undergoing an ophthalmological procedure in which the present compounds are employed would not experience salivation, an increase in heart rate, an increase in blood pressure, sweating or any of the reactions attributable to the cholinergic mechanism. Unlike known antimuscarinics, the present compounds selectively blockade specific cell sites and thereby permit the intended effect at only the site of the desired tissue without inducing the concomitant effect, e.g., increased heart rate, in other tissue.

Most significantly, the compounds of the present invention and particularly QNA can be used to treat certain target tissues which are rich in the $m_1$-AChR without effecting the heart which is characterized by the $m_2$-AChR. For example, the present compounds can be employed for treating bladder conditions such as neurogenic bladder, bed wetting, etc. The present compounds can also be used for treating G-I track conditions such as irritable bowel syndrome; for conditions effecting the brain, the salivary and lacrinal glands and the pancreas. Again, it is noted that among the several advantages, use of the present compounds in these various procedures does not affect the tissue of the heart. Administration of conventional antimuscarinic agents blockade all the receptor sites therefore rendering the conventional compositions substantially useless.

Various preparative procedures are illustrated in the specific examples which are included herein.

The present new compounds form salts with acids when a basic amino function is present. All such salts are useful in the isolation and/or purification of the new products. Of particular value are the pharmaceutically acceptable salts with acids. Suitable acids include, for example, hydrochloric, sulfuric, nitric, benzenesulfonic, toluenesulfonic, acetic, malic, tartaric, and the like that are pharmaceutically acceptable.

The compounds of the present invention can be administered to the host in a variety of forms adapted to the chosen route of administration, i.e., orally, intraveneously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.5% of active compound. The percentage of the compositions and preparations may, of course, be varied and may conveniently be between about 0.5 to about 10% of the weight of the unit. The amount of active compound in such therapeutically useful compositions is such that a suitable dosage will be obtained. Preferred compositions or preparations according to the present invention are prepared so that an oral dosage unit form contains between about 0.1 and 10 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For a better understanding of the present invention together with other and further objects, reference is made to the following descriptions and examples.

EXAMPLE 1

A boiling solution of 13.97 g (0.11 mol) of 3-quinuclidinol in 100 ml of benzene was treated with a 100 mg clean piece of sodium metal. The suspension was refluxed for 30 min and the remaining sodium removed. To the solution was added 16.6 g (0.1 mol) of (±) methyl mandelate in 100 mL of dry benzene. The mixture was refluxed 18 h, cooled, washed repeatedly with water and filtered through a silicon paper. Dried over magnesium sulfate, filtered and the filtrate spin evaporated. The residue was recrystallized from dry acetonitrile. Yield 14.3 g, mp. 128°–130° C. Analysis C,H,N.

EXAMPLE 2

A boiling solution of 2.5 g (20 mmol) of 3-quinuclidinol in 25 mL of benzene was treated with a 100 mg clean piece of sodium metal. The suspension was refluxed for 30 minutes and the remaining sodium removed. A solution of 2.0 g (10 mmol) of methyl atrolactate in 25 mL of benzene was added and the mixture was refluxed for 6 h using Dean-Stark trap. In the process 25 mL of benzene areotrope was distilled off and 25 mL of fresh benzene added. The reaction mixture was washed with water, dried over the $MgSO_4$ and spin evaporated. The residue was charged on a short silica gel column and eluted first with ether then with acetone. The obtained oil 1.2 g was dissolved in AcOEt and 0.4 g of oxalic acid added. The precipitate formed was resuspended in AcOEt containing 10% MeOH and decanted again. The residue was resuspended in AcOEt and filtered. 1.0 g (27%), mp. 189°–196° C. Analysis C,H,N.

EXAMPLE 3

A boiling solution of 2.0 g (16 mmol) of 3-quinuclidinol in 25 mL of dry benzene containing catalytical amounts of sodium 3-quinuclidinoxide was treated with a solution of 1 g (5 mmol) ethyl alpha-ethyl-alphahydroxyphenylacetate in 25 mL of benzene. During the reflux for 16 h under the Dean-Stark trap, 25 mL of benzene areotrope was distilled off and 25 mL of fresh dry benzene was added. The reaction mixture was washed 5 times with water, dried over $MgSO_4$ and the filtrate concentrated in vacuum. The residue was dissolved in ether and treated with 0.3 g of oxalic acid dissolved in ether. The precipitate formed was decanted and resuspended in dry AcOEt. The obtained white powder was dried in vacuum at room temperature to give 0.8 g (42%) of product. Mp. 125°–129° C. Analysis C,H,N.

EXAMPLE 4

A solution of 1.3 g (5.8 mmol) of ethyl alphahydroxy-alpha-propyl-phenylacetate in 25 mL of dry benzene was added to 0.8 g (6.4 mmol) of 3-quinuclidinol in 25 mL of boiling benzene containing catalytical amounts of sodium 3-quinuclidinoxide. The mixture was refluxed under Dean-Stark trap and traces of ethanol formed were removed azeotropically. After 18 h of reflux the reaction mixture was repeatedly washed with water and the organic layer dried over $MgSO_4$. Filtration and concentration in vacuum produced 1 g of oily residue. The residue was charged on a short silica gel column and eluted first with ether then with acetone. Obtained was 0.8 g of an oil which was converted to an oxalate. The precipitate was repeatedly dissolved in hot AcOEt and reprecipitated with petroleum ether to give 0.6 g (38%) of product, mp. 57°–67° C.

MATERIALS AND METHODS

3-Quinuclidinyl benzilate, 3-quinuclidinyl atrolactate and the analogues of QNA were synthesized in our laboratories. Purity was determined by reversed phase high performance liquid chromatography (HPLC), and all compounds gave analyses within 0.4% of the theoretical values. Both QNB and 3-quinuclidinyl atrolactate and its analogues are racemic mixtures, and the remaining analogues contain all four diastereomers.

Tissue Preparation

Hearts were removed immediately upon killing female Sqrague-Dawley rats (cervical dislocation under light ether anesthesia). The ventricular muscle was dissected free of atria, major vessels and fat, and minced with scissors. The tissue was homogenized (Brinkman Polytrol PC-U) in 20 vol. of ice-cold buffer (buffer constituents varied according to study) containing 10% sucrose. The homogenate was filtered through four layers of cheesecloth and used without further preparation (except in the equilibrium dialysis studies). The heart of a mongrel dog was removed, and the left ventricular muscle was dissected free of remaining tissue, fat and vessels, frozen in liquid nitrogen, and stored at −80° until used. One- to two-gram segments from the muscle were prepared as above. Storage for up to 6 months did not change the binding characteristics of the m-AChR. The concentration of $m_2$-AChR in such preparations varied from 0.4 to $1.2 \times 10^{-11}$ M.

The brains of female rabbits (New Zealand Albino, 4–5 lb) were removed immediately upon sacrifice and placed on ice. The caudate nucleus and putamen were dissected free and immediately frozen and stored at −80° until used. Approximately 0.10 to 0.15 g of caudate/putamen (CP) was homogenized in ice-cold buffer as described above and used without further purification. The concentration of $m_1$-AChR in these preparations was similar to that obtained using heart.

Equilibrium Association Constants ($K_{VM}$ and $K_{CP}$) Filtration Assay

Analogues of QNB are dissolved in 95% EtOH at 200-fold the desired assay concentration and 0.025 ml added to 5 ml of Tris buffered 0.9% saline (10 mM, pH 7.4) containing $2 \times 10^{-10}$ M ($^3$H) QNB. The final concentration of EtOH (5%) does not alter receptor binding properties. Competition curves are generated using at least 10 concentrations of inhibitor. Aliquots of 0.1 ml of tissue preparation are added, the mixture vortexed and incubated at ambient temperature for 2 h. Neither increased incubation time nor continuous agitation altered the results. The incubation was rapidly filtered on GF/C filters, washed with 10 ml of ice-cold saline, air dried and counted in a liquid scintillation counter in ACS liquid scintillation mixture. Data were analyzed using the LIGAND programs of Munson and Rodbard (Anal. Biochem. 107, 220 [1979]) using data from at least five determinations (in duplicate) on separate occasions.

Equilibrium Dialysis

Receptor containing tissue (2 g ventricular muscle or 0.15 g caudate/putamen) are solubilized in 0.4% digitonin/0.08% cholate and the 100,000×g supernatant used for receptor assay. Aliquots of 0.3 ml of supernatant are added to 1 cm dialysis tubing and dialyzed for 36 h at 4° C. against a buffer (50 mM $Na_2HPO_4/NaH_2PO_4$, pH 7.4; 1.5 mM EDTA; $10^{-4}$ M phenylmethylsulfonyl fluoride) containing $2\times10^{-10}$ M ($^3$H) QNB and inhibitor at final concentrations from $10^{-5}$ M to $10^{-12}$ M. Samples from the dialysis bags were counted for total activity present. The extent of non-receptor binding and free ligand present in the samples was determined using the LIGAND programs which also provide the equilibrium association constant for the inhibitor.

TABLE I

SELECTIVITY OF 3-QUINUCLIDINYL ALPHA-ALKYL MANDELATES

| Compound of sample ($R_1$ substitutions) | RBI VM[a] | RBI CP[b] | Selectivity[c] |
|---|---|---|---|
| 1 H | 0.134 | 0.94 | 7.0 |
| 2 $CH_3$ | 0.36 | 9.1 | 25.3 |
| 3 $CH_2CH_3$ | 3.45 | 24.5 | 7.1 |
| 4 $CH_2CH_2CH_3$ | 40.4 | 89 | 2.2 |
| 5 $CH_2CH_2CH_2CH_3$ | 55 | 95 | 1.7 |
| QNB[d] | 100 | 100 | 0 |

[a] relative binding index of ventricular muscle ($m_2$-AChR) = $\frac{\text{affinity constant of compound}}{\text{affinity constant of QNB}} \times 100$

[b] relative binding index of caudate/putamen ($m_1$-AChR) = $\frac{\text{affinity constant of compound}}{\text{affinity constant of QNB}} \times 100$

[c] $\frac{\text{RBI CP}}{\text{RBI VM}}$ relative binding index ratio of CP to VM

[d] 3-quinuclidinyl benzilate

We claim:

1. A compound represented by the general formula:

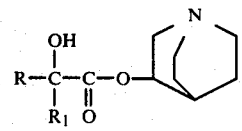

wherein R is unsubstituted phenyl; $R_1$ is hydrogen, and methyl, ethyl, propyl, isopropyl or butyl; and the pharmaceutically acceptable salts thereof.

2. The compound of claim 1 wherein $R_1$ is methyl.

3. The compound 3-quinuclidinyl atrolactate.

4. A selective antimuscarinic composition comprising an antimuscarinic effective amount of a compound represented by the general formula:

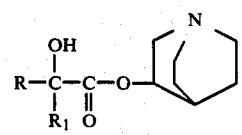

wherein R is unsubstituted phenyl; $R_1$ is hydrogen, and methyl, ethyl, propyl, isopropyl or butyl; and the pharmaceutically acceptable salts thereof, said compound being administered in an amount sufficient to effect the desired blockade of the $m_1$-AChR receptors.

5. The composition of claim 4 having a dosage unit form containing about 0.1 to about 10 mg of said compound.

6. The composition of claim 4 wherein $R_1$ is methyl.

7. A method for selectively antagonizing muscarinic acetylcholine receptors designated $m_1$-AChR comprising the administration of a compound represented by the general formula:

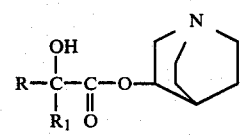

wherein R is unsubstituted phenyl; $R_1$ is hydrogen, and methyl, ethyl, propyl, isopropyl or butyl; and the pharmaceutically acceptable salts thereof, said compound being administered in an amount sufficient to effect the desired blockade of the $m_1$-AChR receptors.

8. The method of claim 7 wherein the compound is administered in an amount from about 1 mg to about 100 mg per kg per day.

9. The method of claim 7 wherein $R_1$ is methyl.

* * * * *